(12) United States Patent
Aboul-Hosn et al.

(10) Patent No.: US 6,234,960 B1
(45) Date of Patent: May 22, 2001

(54) HEART STABILIZER APPARATUS

(75) Inventors: Walid N. Aboul-Hosn; Michael Guidera; William Russell Kanz, all of Sacramento; Richard Milson, Orangevale, all of CA (US)

(73) Assignee: A-Med Systems, Inc., West Sacramento, CA (US)

( * ) Notice: Subject to any disclaimer, the term of this patent is extended or adjusted under 35 U.S.C. 154(b) by 0 days.

(21) Appl. No.: 09/164,397

(22) Filed: Sep. 30, 1998

(51) Int. Cl.[7] .................................................. A61B 17/00
(52) U.S. Cl. ........................... 600/231; 600/201; 600/235
(58) Field of Search ............................. 606/198; 600/201, 600/231, 232, 234, 217

(56) References Cited

U.S. PATENT DOCUMENTS

| 4,492,229 | * | 1/1985 | Grunwald | 606/148 |
|---|---|---|---|---|
| 4,536,893 | * | 8/1985 | Parravicini | 623/3 |
| 4,622,955 | * | 11/1986 | Fakhrai | 600/217 |
| 4,690,134 | * | 9/1987 | Snyders | 601/153 |
| 5,131,905 | * | 7/1992 | Grooters | 600/16 |
| 5,167,223 | * | 12/1992 | Koros et al. | 128/20 |
| 5,702,343 | * | 12/1997 | Alferness | 600/37 |
| 5,964,699 | * | 10/1999 | Rullo et al. | 600/228 |

* cited by examiner

Primary Examiner—Paul J. Hirsch
Assistant Examiner—Michael B. Priddy
(74) Attorney, Agent, or Firm—Jonathan Spangler

(57) ABSTRACT

Methods and apparatus are described to manipulate the position of the heart to provide surgical access to lateral and posterior portions of the heart. A jack apparatus connected to a surgical retractor can be positioned in the surgical cavity to produce a sideways force on the heart. A tripod apparatus can be used to hold up the heart into a desired position. A band can be attached to the heart to rotate its position. Fingers attached to the bottom of a blade on a surgical retractor can be used to manipulate the heart's position.

6 Claims, 13 Drawing Sheets

HEART STABILIZER APPARATUS

FIELD OF THE INVENTION

The present invention is directed to apparatus, systems, equipment and methods for heart bypass surgery.

BACKGROUND OF THE INVENTION

In heart surgery, the patient's sternum is often spread using a surgical retractor. This allows the surgeon access to the patient's heart to perform the necessary procedures. An example of a prior art surgical retractor is given in Koros, et al., U.S. Pat. No. 5,167,223, which is incorporated herein by reference.

In beating heart surgery, the surface of the heart must be stabilized to perform surgical procedures such as bypass graphs. Often, a stabilizing fork which is attached to a surgical retractor is used to stabilize the surface of the heart. Because the heart is a pulsatile contractive muscle, the area for which the bypass is to be performed must be stabilized to allow the surgeon to suture the bypass graph to the target artery.

For some procedures, the current stabilizing fork cannot be properly placed to provide sufficient stabilization of the surgical site. Generally this is so where the target artery is located on the back side of the heart and the heart must be rotated and stabilized. Stabilization forks are not designed to rotate or hold the heart in a rotated position. For this reason, in practice, the stabilizer fork is often removed from the surgical retractor by a surgical assistant and held manually in position on the surface of the heart. A problem with this method is that it places another person within the surgical field, thereby limiting the amount of space the surgeon has available to perform the desired surgical procedures. Devices such as the Octopus from CTS, have been designed to hold the heart in a rotated position and provide stabilization of the surgical site, though they are complicated to set up and require constant attention throughout the procedure.

It is desired to have an improved method and apparatus for positioning and stabilizing the heart during heart surgery.

SUMMARY OF THE INVENTION

The present invention provides apparatus systems and methods which enable heart surgery on all vessels of the heart, but especially on the less accessible lateral and posterior vessels of the heart.

In one embodiment the present invention comprises a stabilizing apparatus that allows for a stabilizing element to apply force from inside the surgical space. In a preferred embodiment, a support is connected to a surgical retractor and positioned within the surgical space. A jack connected to the support is extended so that a stabilizing element at the end of the jack can contact the heart with a sideways, rather than a downward, force on the heart. This provides sufficient stabilizing force for lateral and posterior vessels of the heart.

Another embodiment of the present invention comprises an elastic band that wraps around the heart. Lines attached to the band can be manipulated to maneuver and rotate the heart so as to provide surgical access to the lateral and posterior vessels of the heart. In one embodiment, the lines can be sent to a rotatable assembly to maneuver the band.

Another embodiment of the present invention comprises fingers that can be attached to the bottom of a blade on a retractor arm. The fingers are attached so that they can rotate outward. These fingers can be used to manipulate the heart during heart surgery.

DESCRIPTION OF THE INVENTION

FIGS. 1–5 illustrate a stabilizer apparatus 20 that can be used to apply pressure on portions of the heart during a heart operation.

Figure 1:
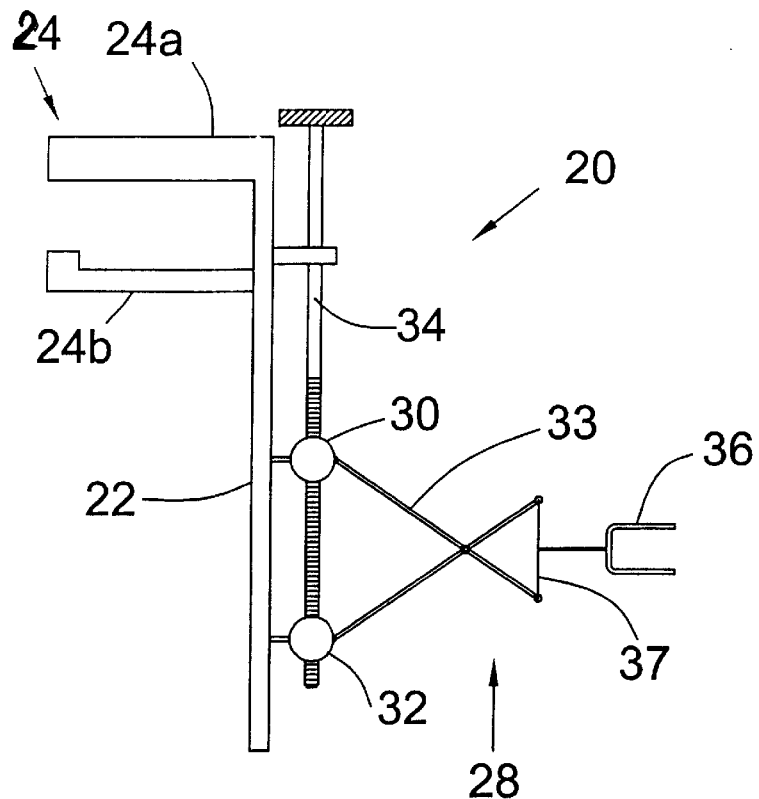
FIG. 1 is a side view of a stabilizer apparatus of the present invention.
Figure 2:
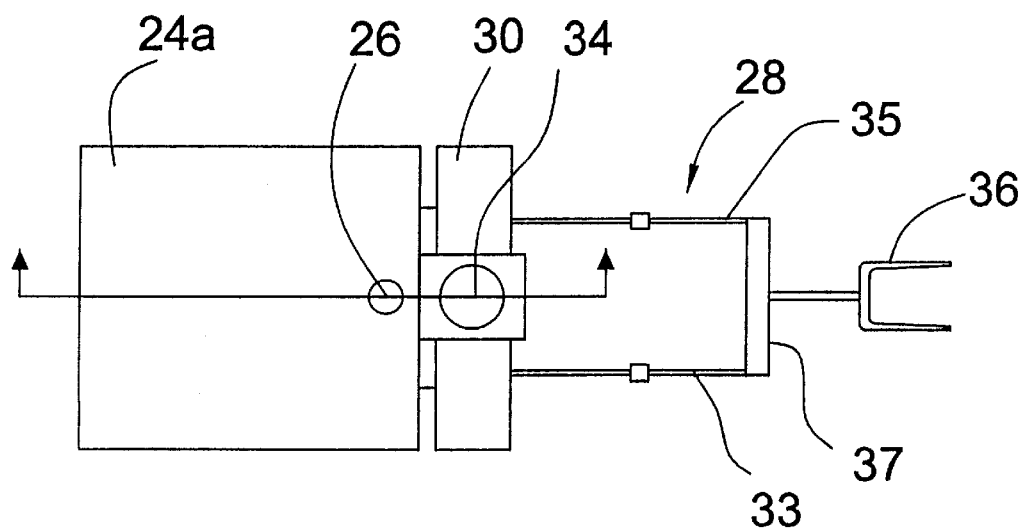
FIG. 2 is a top view of the stabilizer apparatus of FIG. 1.
Figure 3:
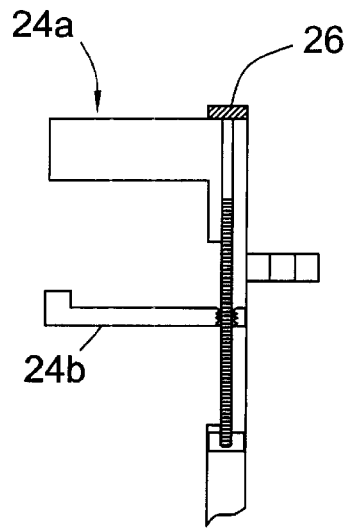
FIG. 3 is a cross-sectional view of a connector portion of the stabilizer apparatus of FIG. 1.
Figure 4:
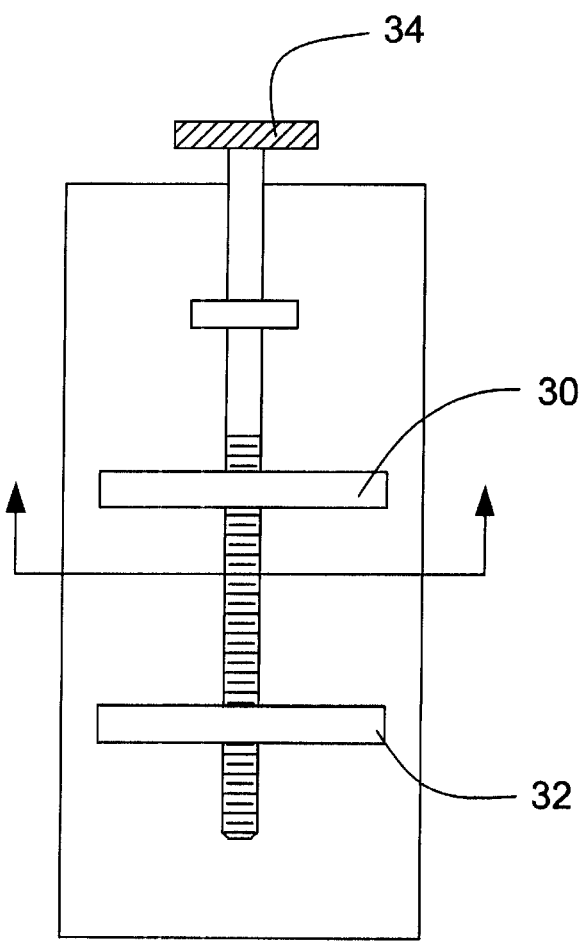
FIG. 4 is a partial view of the stabilizer apparatus of FIG. 1 showing the support, the arms, and the driving means.
Figure 5:
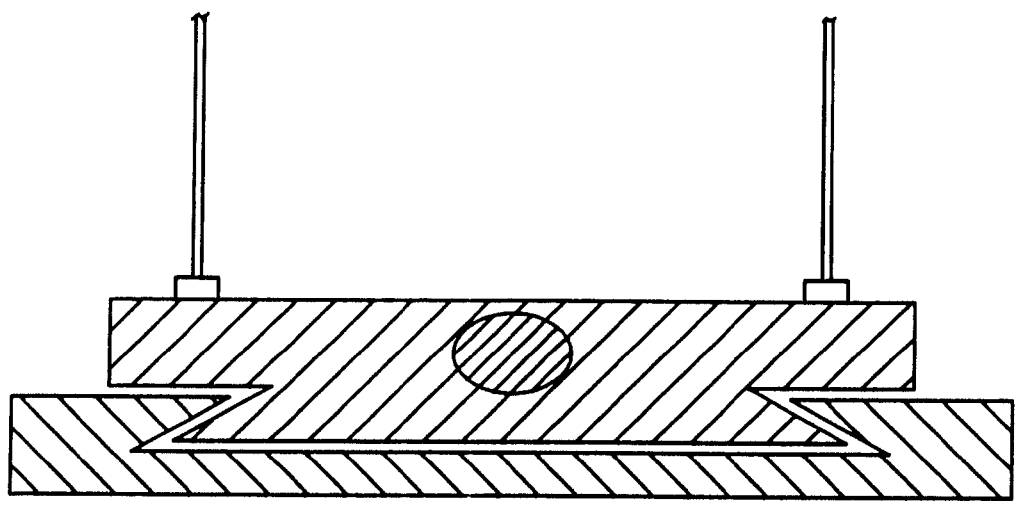
FIG. 5 is a partial cross-sectional view of the stabilizing apparatus of FIG. 1 showing an arm slidably attached to the support.

The stabilizer apparatus 20 is adapted to detachably attach to a surgical retractor. The clamping mechanism 24 at the proximal end of the support 22 comprises first and second arms 24a and 24b. First arm 24a is integrally affixed to vertical support member 22 of the stabilizer apparatus 20. Second arm 24b is slidably affixed to vertical support member 22. Second arm 24b moves proximally and distally with respect to first arm 24a. In a preferred embodiment, the second arm 24b is disposed within channel 22a of support 22 as illustrated in FIG. 5, and displaced by screw mechanism 26 as illustrated in FIG. 3.

During use, stabilizer apparatus 20 is clamped to a surgical retractor external to the surgical cavity. The distal end of the stabilizer apparatus is positioned within the surgical cavity. As illustrated in FIGS. 1–5 stabilizer apparatus can stabilize the surface of the heart during a surgical procedure. Looking at FIGS. 1 and 2, jack 28 is disposed adjacent to the distal end of support 22. Stabilization mechanism consists of guide rods 30 and 32, a screw 34 for driving guide rods 30 and 32, scissor assemblies 33 and 35, base 37, and stabilizing element 36. The driving means, screw 34, is rotated either clockwise or counterclockwise to displace guide rods 33 and 35. As guide rods 33 and 35 are displaced about a vertical plane, scissor assembly 33 and 35 moves within a horizontal plane perpendicular to the vertical plane in which the driving mechanism is disposed. The distal end of the scissor assembly contains a base 37 for attaching a stabilization element 36.

The stabilization element 36 may be in the form of a stabilizer fork with 2 arms. Alternately, the stabilization element 36 may be formed in many different shapes, such as, closed loops, square, or other geometric shapes.

The advantage of the stabilizing apparatus of the present invention is that the stabilizing force can be provided sideways in the surgical cavity rather than downwards into the surgical cavity. In prior systems an adequate stabilizing force can not be supplied when the surgical site is not on top of the heart when the heart is rotated. The stabilizing forks tend to slip off of the side of the heart. In the present invention, the stabilizing force will be substantially perpendicular to the side of the heart. Thus the stabilizing element will not slip off of the heart.

Figure 6:
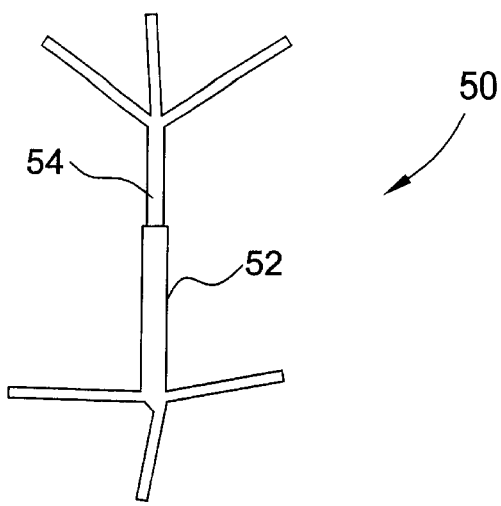
FIG. 6 is a perspective view of a heart supporting apparatus of the present invention.
Figure 7:
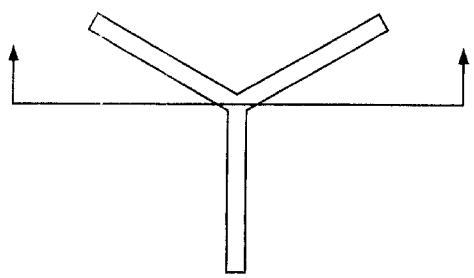
FIG. 7 is a view of the arms of the supporting apparatus of FIG. 6.
Figure 8:
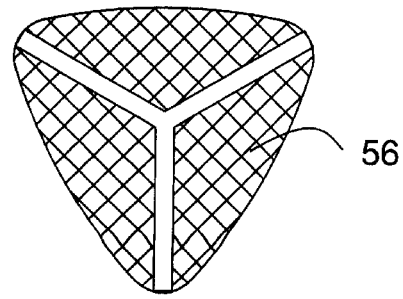
FIG. 8 is a view of the multi-arm portion of a heart supporting apparatus with a flexible mesh positioned between the arms.
Figure 9:
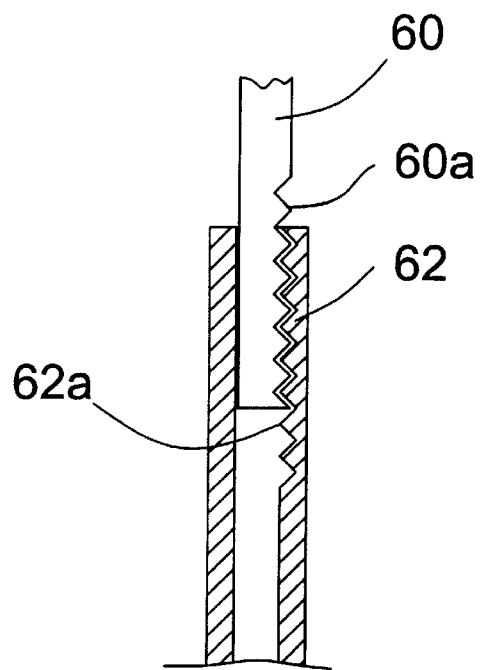
FIGS. 9–11 are cross-sectional views illustrating the connection of the base and multi-arm portion of the heart supporting apparatus.

As illustrated in FIGS. 6–12, in one embodiment of the present invention, a tripod stabilizer 50 is adapted to be placed within the surgical site to stabilize and hold an organ in a translated position. As illustrated in FIGS. 6–8 tripod stabilizer consists of first and second bodies. The bodies are a base 52 and multi-arm portion 54. The base 52 and multi-arm portion 50 are preferably made of least 3 movable arms. In use the patients organ is moved and held while tripod stabilizer is placed in a desired position. The arms on first and second end of tripod stabilizer are moved into a desired pattern to for supporting the organ. As illustrated in FIG. 8 a flexible mesh 50 may be disposed between the arms to provide further support and to limit the movement of the flexible arms. The first and second end of tripod stabilizer move in relation to each other. As illustrated in FIG. 9, in one embodiment the proximal end of one of the tripods is adapted to receive the distal end of the other tripod. As illustrated in FIG. 9, one tripod end 60 is inserted into another tripod end 62, serrated teeth 60a and 62a on each respective body engage, thereby the overall length of the assembly 50 may be adjusted as necessary.

Figure 10:
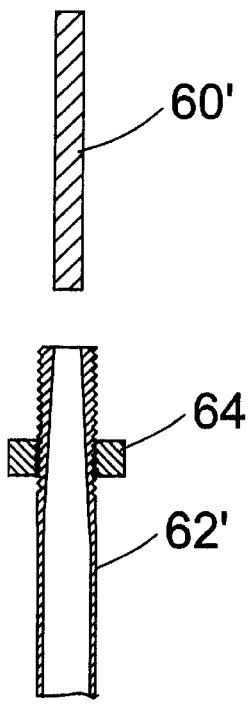
Figure 11:
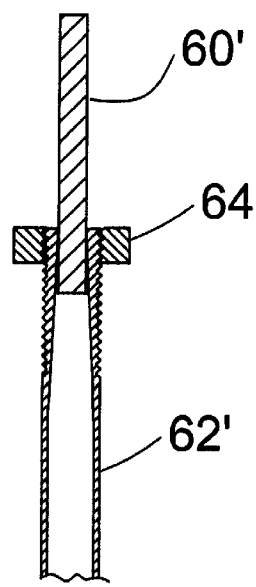

A alternate embodiment is illustrated in FIGS. 10–11. Tripod end 62 is generally hollow and has a tapered inner surface. A locking collar 64 is disposed adjacent the tripod end 62'. The exterior surface of the second body contains threads which engage the threaded locking collar 64. In use the tripod end 60' is inserted into the tripod end 62' and the threaded locking collar 64 is advanced over the threads to lock tripod end 60' into position.

Figure 12:
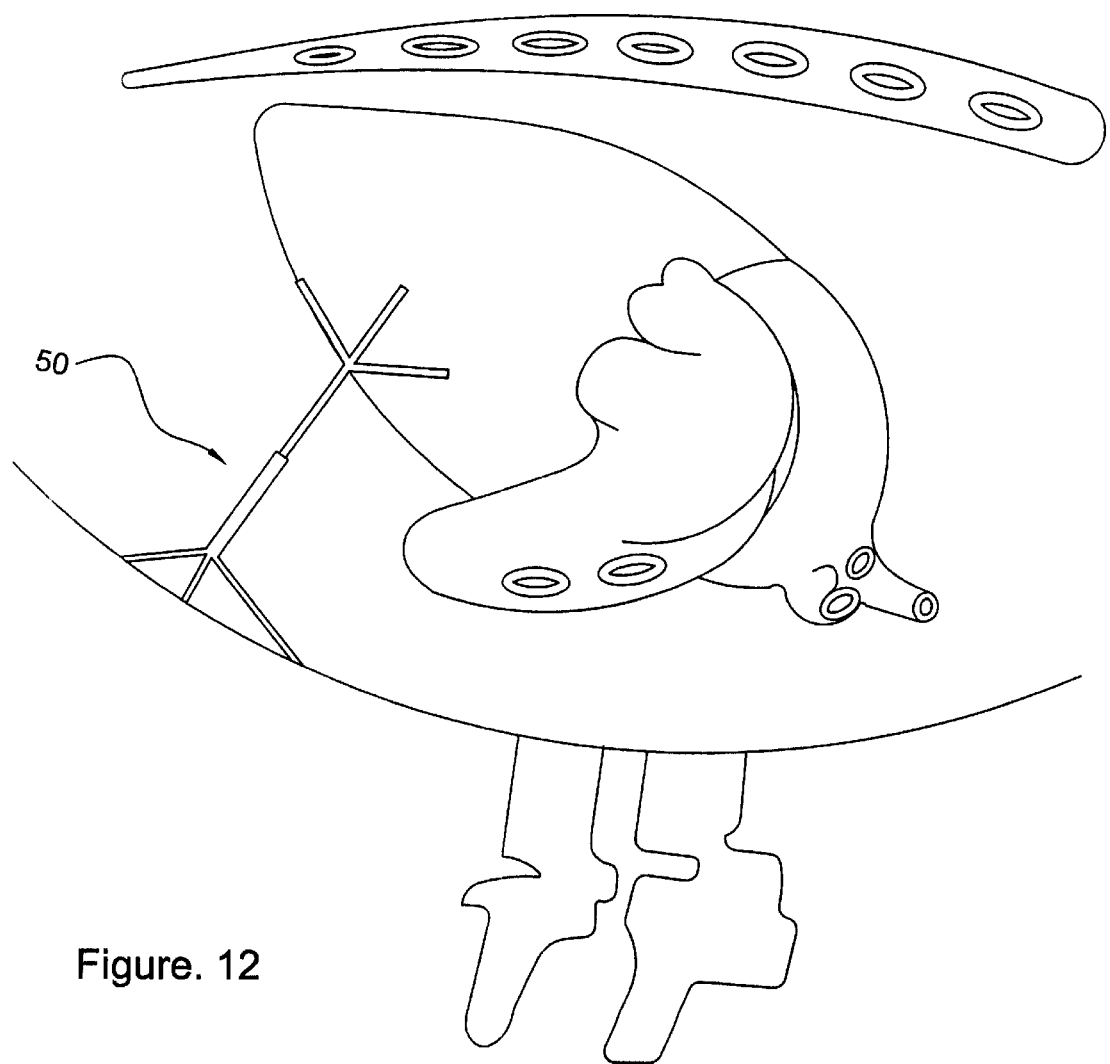
FIG. 12 is a diagram illustrating the positioning of the heart using the heart supporting apparatus of FIG. 6.

As illustrated in FIG. 12 tripod stabilizer 50 can be used to support and stabilize a region of the heart to allow the physician to perform a surgical procedure on the desired area.

Figure 13:
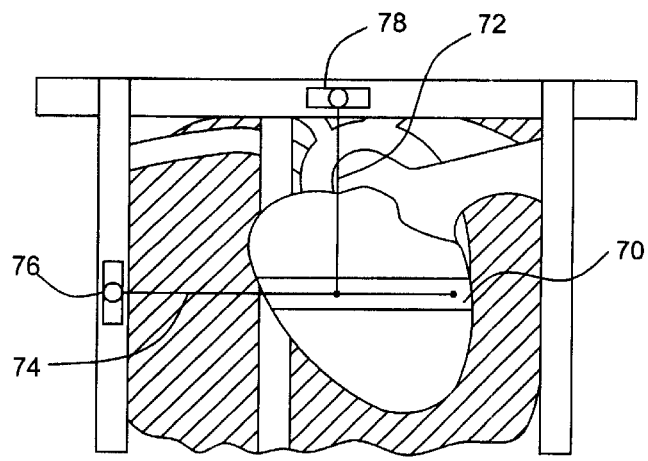
FIGS. 13 and 14 are diagrams illustrating a band with attached lines to rotate the heart.
Figure 15A:
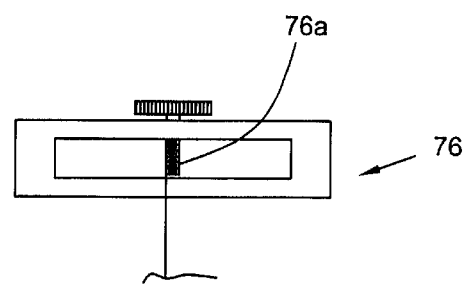
FIGS. 15A–C are diagrams illustrating the rotatable assembly for use with the apparatus of FIGS. 13 and 14.
Figure 14:
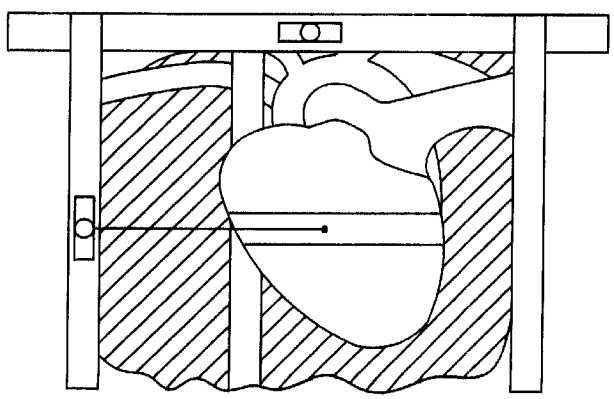
Figure 15B:
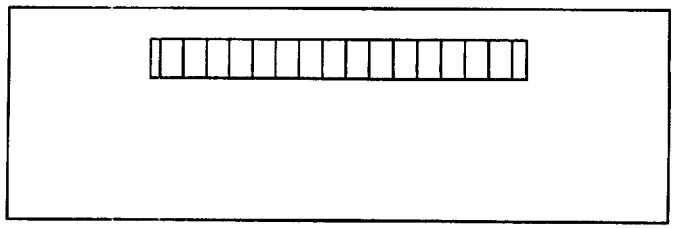
Figure 15C:
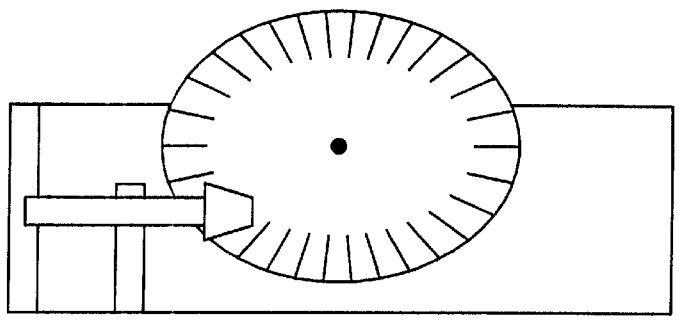

FIGS. 13–15 illustrate a device for rotating and supporting the heart while performing heart surgery. A band 70 is placed about the circumference of the heart. This band 70 is preferably elastic. Flexible lines 72 and 74 are attached to the band disposed about the heart. Line 74 is preferably attached as far away from the rotating device 76 so that you can obtain maximum rotation of the heart while performing the surgery. The proximal end of the line 74 is attached to the rotating device 76. As illustrated in FIG. 15A rotating device 76 preferably comprises a rotatable rod 76a which the lines can wrap around when the rod 76a is rotated.

The lines 72 and 74 are placed on the band 70 in a position away from the rotating devices 76 and 78. As illustrated in FIG. 14., the lines are tightened by rotating rod 76a in rotation device 76.

The means for rotating the heart may be moved about the retractor depending upon the axis of desired rotation. Further the band disposed about the heart may not be necessary. Instead sutures can be placed through the exterior surface of the heart muscle thereby eliminating the requirement of placing a band around the heart.

Figure 19:
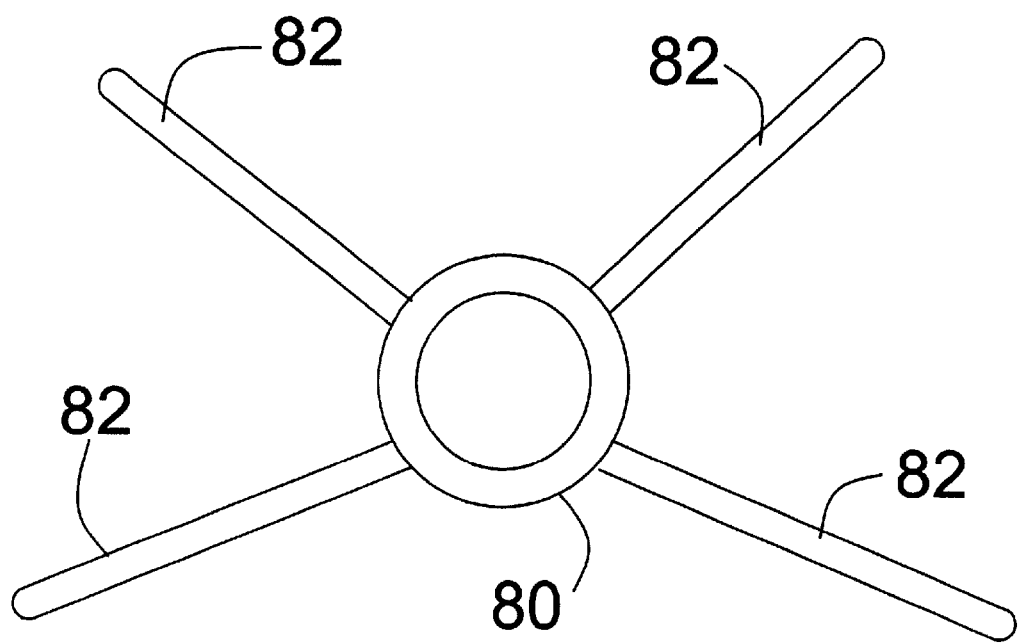
FIG. 19 is a diagram of an alternate embodiment of a band with straps for manipulating the heart.

FIG. 19 shows an alternate embodiment in which a band 80 is connected to straps 82. The band 80 is wrapped around a portion of the heart. In one embodiment the band 80 is wrapped around the tip or apex of the heart.

The straps 82 in one embodiment use microhooks or are adapted to receive microhooks, such as in a velcro system, so that the straps can be secured to position band 80 and thus the heart.

Figure 20:
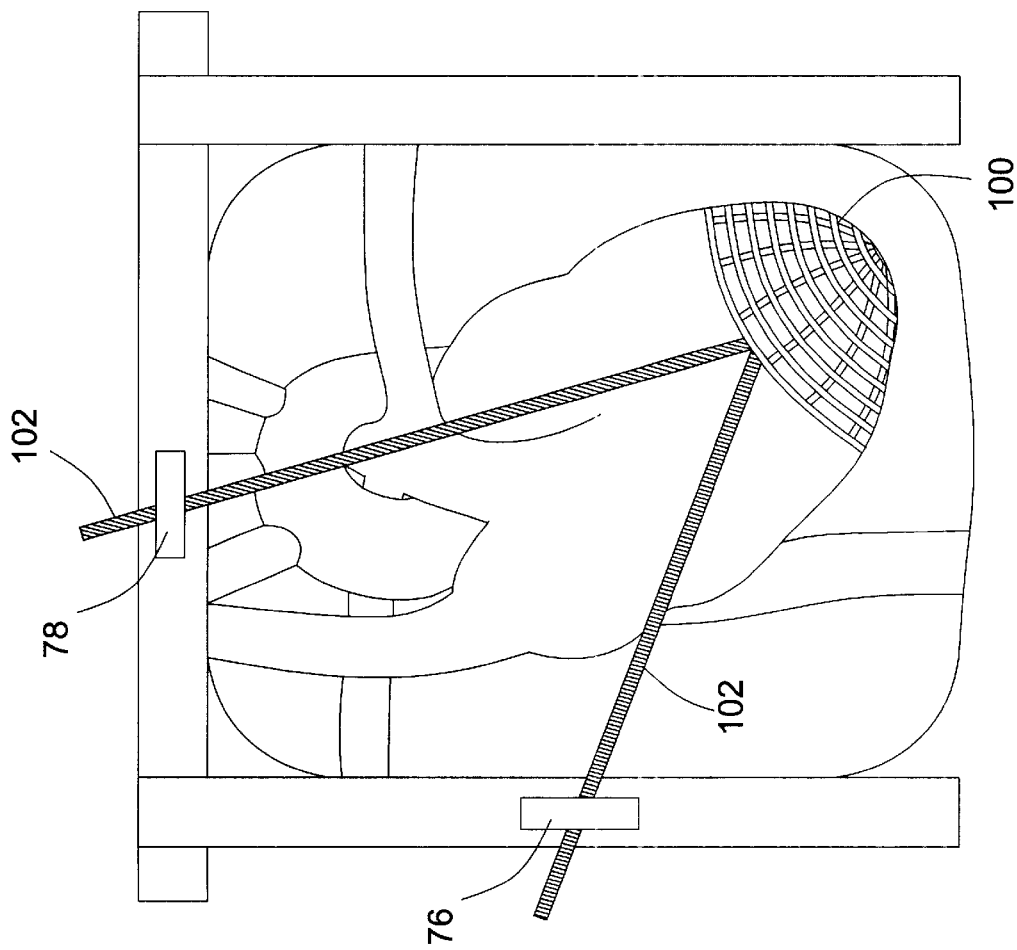
FIGS. 20 and 21 are diagrams illustrating a web for attaching to the heart.
Figure 21:
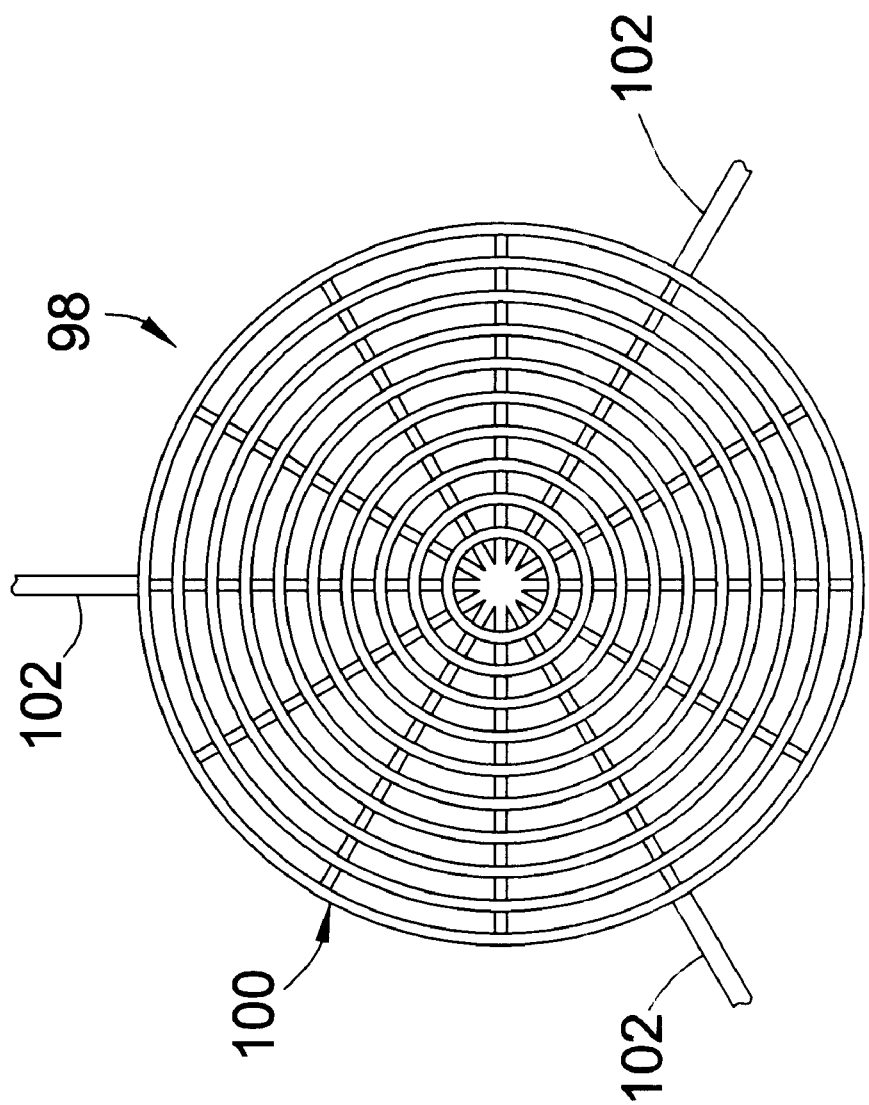

As shown in FIGS. 20 and 21, an alternative embodiment to placing a band around the heart, is to place a webbed or strapped net around the apex of the heart. Apparatus 98 includes web 100 and lines 102. Lines 102 are preferably flexible and can be attached to the rotating device 76 on the surgical retractor. The webbing or netting can be cut away if it covers the desired surgical site. The web is preferably designed so that if a portion is cut from the netting, the cut will not expand.

Figure 22:
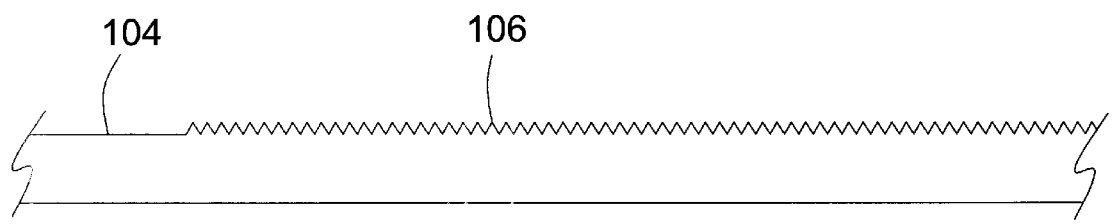
FIG. 22 is diagram of a flexible line with teeth.
Figure 23:
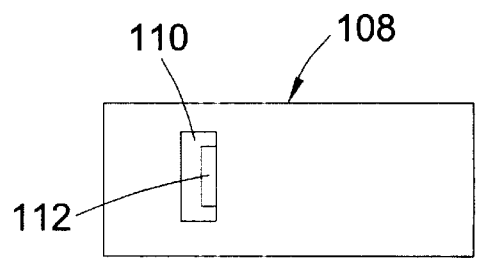
FIG. 23 is a diagram of a locking mechanism.

As shown in FIGS. 22–24, a further design for the flexible lines and locking mechanism is a slip lock mechanism. Flexible lines 104 includes a plurality of raised cross-members 106 spaced along its length, each cross-member being in the shape of a ratchet tooth. Locking mechanism 108 includes a strap accepting channel 110 having an angled locking face 112 for engaging with one of the raised cross members 106. In use, after the proximal end of the flexible strap 104 is inserted into locking members and the insertion force is relaxed, the force on the flexible line 104 by virtue of its configuration causes one of the raised cross-members to abut against the angled locking face 112, to lock the flexible strap in place. The angled locking face 112 may be a flexible tooth that allows the strap to move if sufficient force is applied. Alternately, the flexible tooth may be spring loaded so that it can deflect.

Figure 16:
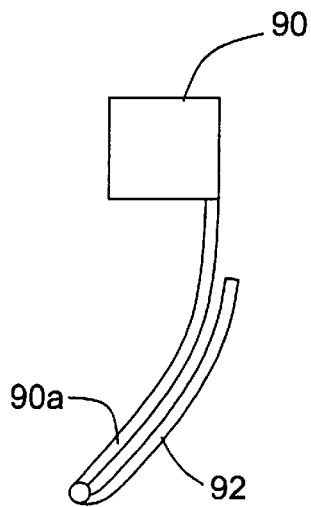
FIG. 16 is a front view of a retractor arm showing fingers for manipulating the heart.
Figure 17:
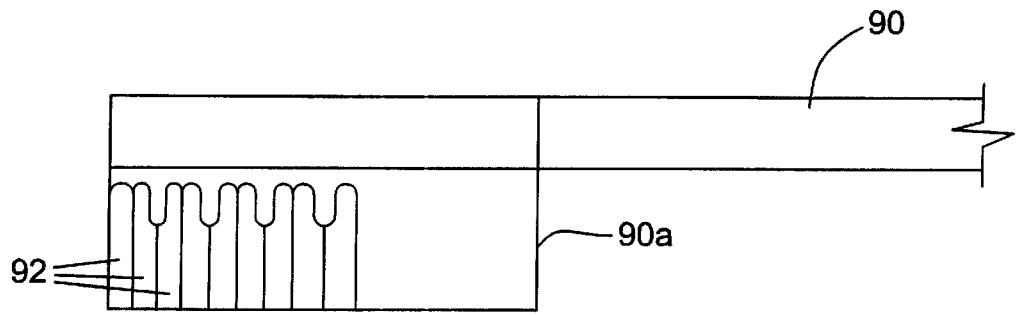
FIG. 17 is a side view of the retractor arm with fingers of FIG. 16.
Figure 18:
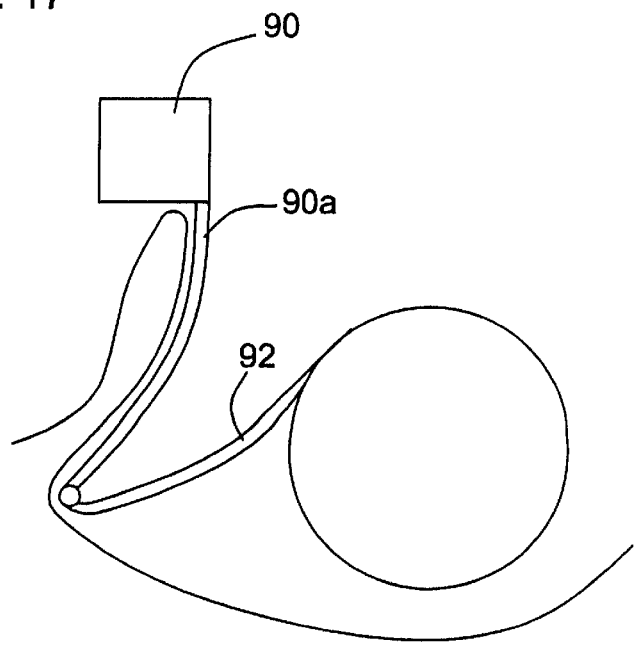
FIG. 18 is a diagram illustrating the positioning of the heart with the fingers attached to the retractor arm.

As illustrated in FIGS. 16–18 a retractor arm 90 includes a blade 90a. When the retractor is used to spread and hold open the patients sternum, the blade 90a is placed against the patient's sternum and ribs and within the chest cavity. During surgical procedures such as heart surgery, it is desirable to support and stabilize the heart in order to perform coronary artery graph anastomosis or other procedures. The present embodiment provides a means for supporting the heart during surgical procedures. A series of flexible, malleable fingers 92 are displaced along the distal end of the retractor blade. When it is desired to support an area on the heart to perform, an anastomosis or to hold the heart in a displaced position the finger(s) 92 are displaced from resting position and moved into a desired support position, or the finger(s) 92 may be slidably attached to the distal end of the retractor blade. Therefore when it is desired to displace the heart from resting position finger(s) 92 may be moved into a desired position adjacent to the surface of the heart.

The distal end of the fingers may be formed with different geometric shapes, the ends may be blunt, rounded, or a combination of geometric shapes as illustrated in FIG. 17. Fingers have been positioned on a surgical retractor in the past but typically these fingers have been positioned on top of the retractor arm to hold skin away from the surgical field. By attaching fingers 92 at the bottom of the blade 90a the fingers can be used to manipulate the heart's position.

Beating heart bypass surgery is desirable because it can avoid the necessity of placing the patient on a full cardiopulmonary bypass (CPB) system. This application describes methods and apparatuses to manipulate and stabilize the heart so as to provide surgical access to posterior heart vessels which may be useful for beating heart surgery.

The application "Apparatus And Methods For Beating Heart Bypass Surgery", Ser. No. 09/079836 filed May 15, 1998, which is incorporated herein by reference, describes pump and cannula systems to enable safe beating heart surgery on lateral and posterior blood vessels, as well as anterior blood vessels, without the necessity of using CPB. The systems of that application describe providing support for primarily the right side of the heart by internal cannulation in order to prevent the collapse of the right side of the heart and to maintain adequate pulmonary blood flow from the beating heart. This allows the methods and apparatus of the present invention to manipulate and stabilize the heart so as to provide surgical access to the anterior, lateral and posterior heart vessels during beating heart surgery.

While the present invention has been described with reference to the aforementioned application, this description of the preferred embodiment and method is not meant to be construed in a limiting sense. It should be understood that all aspects of the present invention are not limited to the specific depictions, configurations, or relative proportions set forth herein which depend upon a variety of conditions.

Various modifications in form and detail of the various embodiments of the disclosed invention, as well as other variations of the present invention, will be apparent to a person skilled in the art upon reference to the present disclosure. It is therefore contemplated that all attendant claims shall cover any such modifications or variations of the described embodiments as following within the true spirit and scope of the present invention.

What is claimed is:

1. A cradle for supporting a heart within a chest cavity during cardiac surgery, comprising:

a band adapted to wrap around a portion of said heart so as to leave exposed all areas of said heart other than where said band is positioned; and at least one connecting element connected to said band for holding heart in a preselected position within said chest cavity to provide surgical access to lateral or posterior heart vessels of said heart.

2. The cradle of claim 1, wherein said connecting elements are connected to a surgical retractor.

3. The cradle of claim 2, wherein said connecting elements are connected to rotatable rods on said surgical retractor.

4. The cradle of claim 1, wherein said band is made of an elastic material.

5. The cradle of claim 1, wherein said band is adapted to wrap around the tip of said heart.

6. The cradle of claim 1, wherein said connecting elements are made of an elastic material.

* * * * *